United States Patent [19]

Schulze et al.

[11] Patent Number: 4,951,861

[45] Date of Patent: Aug. 28, 1990

[54] SURGICAL STAPLER PRESSURE REGULATOR

[75] Inventors: Dale Schulze, Lebanon, Ohio; Bela Vincze, Flemington, N.J.; James Bedi, Cincinnati, Ohio; Jess Deniega, Flemington; Jack Pedlick, Butler, both of N.J.; William Fox, New Richmond, Ohio

[73] Assignee: Ethicon, Inc., Somerville, N.J.

[21] Appl. No.: 294,222

[22] Filed: Jan. 9, 1989

[30] Foreign Application Priority Data

Jan. 15, 1988 [GB] United Kingdom ............... 8800909

[51] Int. Cl.[5] ............................................. A61B 17/00
[52] U.S. Cl. ...................................... 227/178; 227/8; 227/19; 227/130
[58] Field of Search ............... 227/8, 19, 130, 179, 227/175, 176, 177, 178

[56] References Cited

U.S. PATENT DOCUMENTS

| 3,613,507 | 10/1971 | Smith ........................... 91/398 |
| 3,618,842 | 11/1971 | Bryan ........................... 227/138 |
| 3,638,652 | 2/1972 | Kelley .......................... 227/179 |
| 3,643,851 | 2/1972 | Green et al. ................... 227/19 |
| 3,662,939 | 5/1972 | Bryan ........................... 227/19 |
| 3,717,294 | 2/1973 | Green ........................... 227/19 |
| 3,784,077 | 1/1974 | Burke, Jr. et al. ............. 227/8 |
| 3,815,476 | 6/1974 | Green et al. ................... 91/410 |
| 3,836,116 | 9/1974 | Noiles .......................... 91/398 |
| 3,837,555 | 9/1974 | Green ........................... 227/130 |
| 4,264,028 | 4/1981 | Austin .......................... 227/8 |
| 4,331,277 | 5/1982 | Green ........................... 227/19 |
| 4,349,028 | 9/1982 | Green ........................... 227/19 |
| 4,407,432 | 10/1983 | Shichman ....................... 222/54 |
| 4,527,724 | 7/1985 | Chow et al. .................... 227/8 |
| 4,540,110 | 9/1985 | Bent et al. .................... 227/8 |
| 4,605,004 | 8/1986 | Di Giovanni et al. .......... 128/334 R |
| 4,821,941 | 4/1989 | Cotta ........................... 227/130 |

Primary Examiner—Paul A. Bell
Attorney, Agent, or Firm—Paul A. Coletti

[57] ABSTRACT

A surgical stapling instrument is provided which employs a highly pressurized gas as its source of energy. The highly pressurized gas is conducted to means for indicating the presence of the pressurized gas and to a pressure regulator. The pressure regulator controllably develops gas pressurized to a desired operating pressure. The pressure regulator supplies gas at a fixed or variable pressure to a tissue clamping mechanism and to the trigger mechanism of the instrument. In response to actuation of the trigger mechanism gas at the desired stapling pressure is supplied to a stapling mechanism. In a preferred embodiment, pressurized gas is maintained at the stapling mechanism until the trigger mechanism is reset for a subsequent stapling procedure.

23 Claims, 8 Drawing Sheets

SURGICAL STAPLER PRESSURE REGULATOR

This invention relates to surgical staplers for implanting mechanical surgical fasteners in the tissue of a patient, and, in particular, to surgical staplers which are powered by pressure regulated gas.

Surgical staplers which implant surgical fasteners using the force of pressurized gas are known in the art, and are described in U.S. Pat. Nos. 3,837,555; 3,836,116; 3,815,476; 3,717,294; 3,662,939; 3,643,851; 3,618,842; 3,613,507; 4,407,432; 4,439,028; and 4,331,277, among others. In the instruments shown in these patents, a cylinder of pressurized gas is contained in the handle of the instrument. Gas from the cylinder is conducted to a power unit at the rear of the handle, where the pressurized gas is applied to the proximal end of a mechanical linkage arrangement. The mechanical linkage is connected to a staple cartridge at the distal end of the instrument. When the trigger on the handle is depressed, pressurized gas actuates the mechanical linkage to implant a staple from the distally located cartridge.

All of the instruments shown in the above patents deliver a single staple upon each actuation of the instrument. It would be desirable for a pneumatic stapler to implant several staples at each actuation of the instrument, such as is performed by the linear stapler shown in U.S. Pat. No. 4,527,724. The instrument of this invention is capable of implanting one or more rows of staples upon each actuation of the instrument.

In the pressurized gas staplers described in the above patents, the pressure of the gas contained in the cylinder is chosen to provide the operating force required by the mechanical linkage arrangement. Generally, the gas pressure is on the order of 100 p.s.i. A valving system conducts the pressurized gas from the cylinder to the linkage upon demand, whereby the linkage arrangement is actuated by the 100 p.s.i. gas pressure. A disadvantage of such a system is that as the pressurized gas in the cylinder becomes depleted, the force applied to the mechanical linkage system declines, until a point is reached at which the force of the applied gas is insufficient to actuate the stapling mechanism.

A solution to this dilemma is to employ cylinders which are highly pressurized with $CO_2$ gas. Such cylinders are commercially available, and are generally pressurized to a pressure of about 800 p.s.i. At this pressure the $CO_2$ is in a liquified state and as it is released from the cylinder under atmospheric pressure it boils to the gaseous state. These cylinders will advantageously provide pressurized gas well in excess of 100 p.s.i. for as long as $CO_2$ remains in the cylinder in the liquified state.

However, the high pressure of these cylinders is well in excess of that which is desirably employed in a surgical stapling instrument. Accordingly, if such cylinders are to be employed in a surgical stapler, means must be provided to controllably reduce the high pressures of the $CO_2$ gas to a lower, more acceptable level.

In accordance with the principles of the present invention, a surgical stapling instrument is provided which employs a highly pressurized gas as its source of energy. The highly pressurized gas source is located in the handle of the instrument and is conducted to means for indicating the presence of the pressurized gas and to a pressure regulator. The pressure regulator controllably develops gas pressurized to a desired operating pressure when pressurized by the highly pressurized gas. The pressure regulator supplies gas at the desired operating pressure to a distribution mechanism. In response to a first actuation of the stapling instrument the distribution mechanism operates to direct gas at the desired operating pressure to a tissue clamping mechanism in the stapler head. In response to a second actuation of the instrument the distribution mechanism operates to direct gas at the desired operating pressure to a stapling mechanism in the stapler head.

In a second embodiment a pressure regulator supplies gas at a variable, controlled pressure, which is applied to the clamping mechanism. Once the stapler has been adjusted to develop stapling pressure, the trigger may be actuated to staple the clamped tissue. Following stapling at least a minimal pressure is supplied to the stapler head until the instrument is reset.

Figure 1:
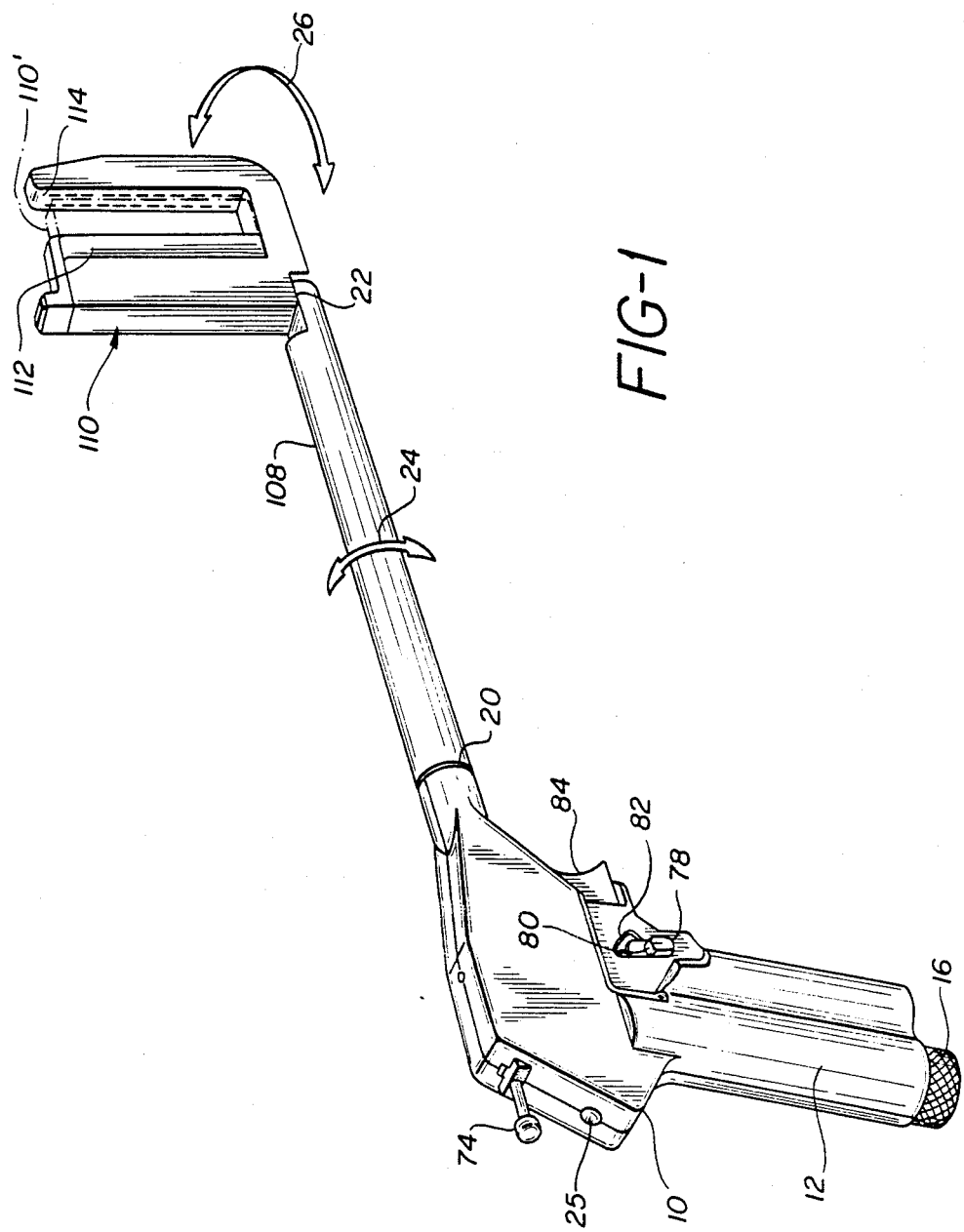
FIG. 1 is a perspective view of a surgical stapler constructed in accordance with the principles of the present invention.

Referring first to FIG. 1, a pneumatically actuated surgical stapler of the present invention is shown. The stapler includes three major components: a handle portion 10, a shaft portion 108, and a stapler head 110. The three components are joined at their interconnecting points by pneumatic quick-disconnect fittings which allow the components to be disconnected and interchanged with shafts and stapler heads of other configurations. Also located at the joints 20 and 22 are pneumatic rotatable unions which allow free rotation of the major components of the stapler with respect to each other, as indicated by the arrows 24 and 26. Specifically, the shaft 108 is free to rotate completely about its axis at the joint 20 as indicated by arrow 24. The stapler head 110 is free to rotate greater than 200° about an axis which is normal to the axis of the shaft 108, as indicated by arrow 26.

A cylinder of pressurized gas is inserted into the lower portion 12 of the handle 10 by removing the cap 16 and inserting the cylinder into the handle. Once the cylinder has been inserted and the cap 16 tightened, gas from the cylinder is released and flows to a pressure regulator in the handle. The release of gas from the cylinder arms the stapler and causes a button 25 to extend a short distance out the rear of the handle, indicating to the user that the stapler is pressurized.

The first step in a stapling procedure is to clamp the tissue to be stapled between the jaws of the stapler head 110. The tissue is located between the jaws, and a slide 74 which extends from the rear of the stapler is depressed. When the slide is pressed forward, pressurized gas is allowed to flow to the stapler head through a first gas line to clamp the tissue between the jaws of the stapler head. As soon as the slide 74 is released, it slides back to its illustrated extended position by spring force. The position of the rearward portion of the stapler head after clamping is shown in phantom at 110' in FIG. 1.

Staples in a cartridge 112 may then be driven through the clamped tissue by depressing the trigger 84 of the handle. Before the trigger can be depressed, however, a trigger safety 78 must be moved upward in its slot 80 from the position shown in FIG. 1 and rotated into a forward extension 82 of the slot 80. This safety mechanism prevents inadvertent placement of the staples before the user is ready to do so. After the trigger safety 78 has been moved up and rotated forward the trigger may be depressed to implant the staples in the tissue, either by clinching the legs of the staples against an anvil 114 in the stapler head 110 or by interlocking the legs of the staples with connecting staple receivers located in the position of the anvil. As the trigger 84 is depressed, the trigger safety is rotated back to its more vertical position and slides downward in slot 80 by spring force.

The shaft 108 and stapler head 110 shown in FIG. 1 are more fully described in concurrently filed U.S. Pat. application Ser. No. 294,523, filed Jan. 9, 1989, entitled "PNEUMATICALLY ACTUATED SURGICAL STAPLER HEAD."

Figure 2:
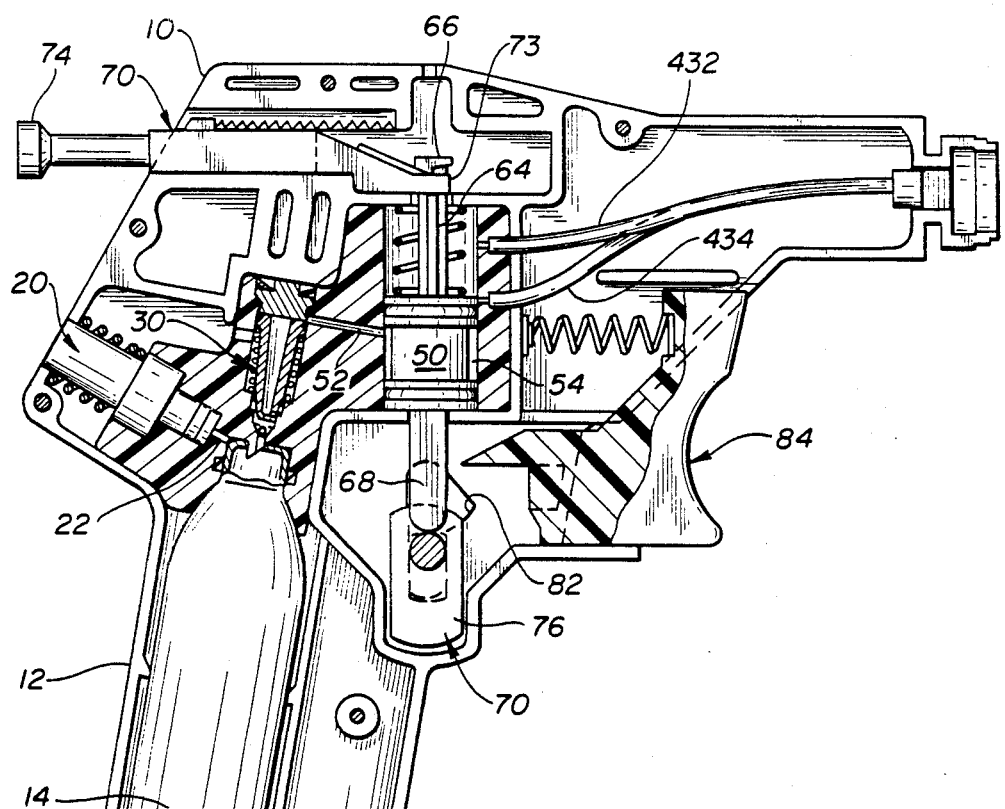
FIG. 2 is a cross-sectional view of the handle portion of a gas powered surgical stapler constructed in accordance with the principles of the present invention.
Figure 3:
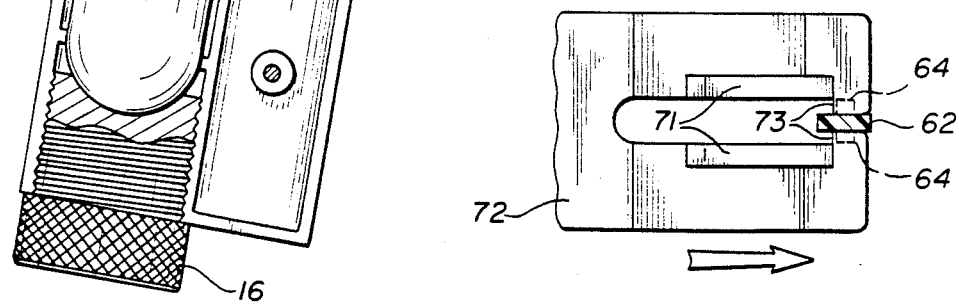
FIG. 3 is a partial plan and cross-sectional view of one of the safety mechanisms associated with the distribution mechanism.
Figure 4A:
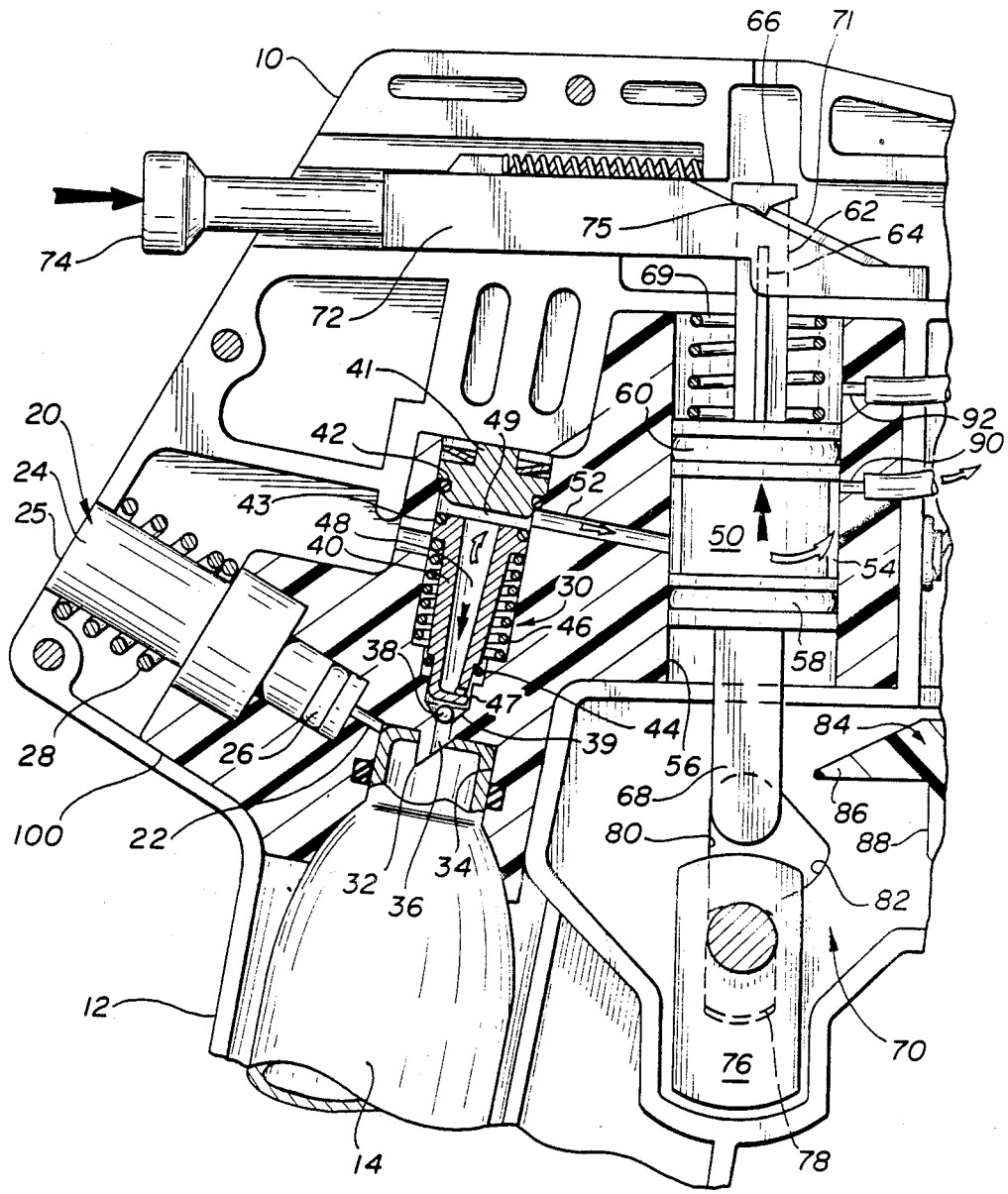
FIGS. 4a–4c show portions of the mechanisms of FIG. 3 during specific phases of the operating sequence of the gas powered surgical stapler.
Figure 4B:
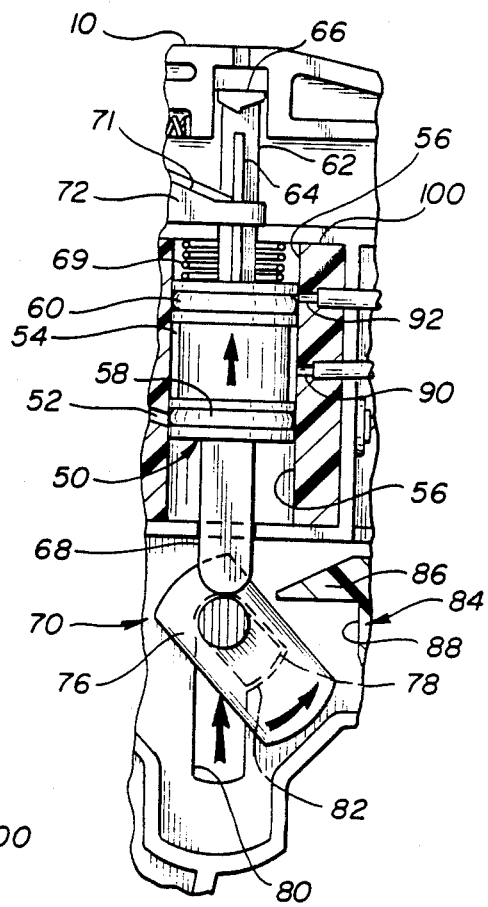
Figure 4C:
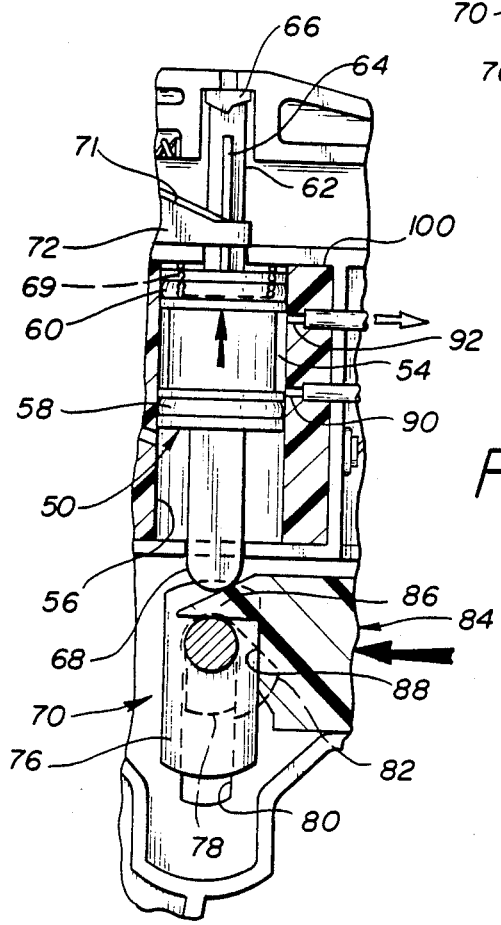

A pneumatic pressure regulation and distribution system suitable for the development of pressure-regulated gas for operation of the stapler head of FIG. 1 is shown in FIGS. 2 and 3, and in various stages of operation in FIGS. 4a–4c. With reference to these FIGURES and in particular FIG. 2, the handle portion 10 of a gas powered stapler of the present invention is shown. The handle portion 10 is a subassembly which contains a pressurization indicator 20, a pressure regulator 30, a pressure distribution spool 50, and firing sequencing mechanism 70. The lower pistol grip section 12 of the handle 10 contains a compartment for a pressurized $CO_2$ gas cylinder 14. The cylinder is inserted into the pistol grip section from the bottom, and a threaded cap 16 is tightened to secure the cylinder in its compartment. As the cap is tightened, a spike 32 of the pressure regulator, shown in detail in FIG. 4a, pierces the top of the cylinder to release pressurized gas into the stapler. The pressurized gas is released at the cylinder pressure of approximately 800 p.s.i. and initially the gas pressurizes a chamber 34 where the spike is located. This gas pressure passes through a passageway 22 to pressurization indicator 20. The pressurization indicator 20 includes a cylinder 24 located in a chamber at the rear of the handle and sealed in the chamber by an O-ring 26. Prior to pressurization the end 25 of the cylinder is flush with the outer surface of the handle, and is retained in this position by the force of a spring 28. The pressurized gas overcomes the spring force and extends the end 25 of the cylinder a short distance outside the handle. The circumference of the cylinder is preferably distinctly colored, and this colored region becomes visible when the cylinder extends outward due to the pressure of the gas. This indicates to the user that the stapler is pressurized and is now operable. The spring force is chosen to overcome inadequate gas pressurization as the cylinder empties. For instance, when the gas pressure falls below about 350 p.s.i., the spring force will overcome the gas pressure and the end 25 of the pressurization indicator will recede back into the handle, thereby providing the user with an indication that the gas cylinder must be replaced.

Pressurized gas also passes through a passageway 36 to pressure regulator 30. The pressure regulator includes a ball 38, a central cylinder 40 with O-ring seals 42, 43 and 44, and a spring 46. A central passageway 48 extends through the cylinder 40 and connects a lower chamber 47 containing ball 38 with an upper chamber 49 above the cylinder 40. When the ball 38 is located as shown in FIG. 4a at the bottom of the lower chamber 47 it is positioned on a valve seat 39 so as to seal the opening of passageway 36 into the lower chamber 47.

When the pressurized gas from the cylinder 14 begins flowing through passageway 36 the gas pressure forces the ball 38 up from its valve seat 39 and the gas starts to fill the lower chamber 47. The gas also begins to pass through the central passageway 48 and starts to pressurize the upper chamber 49. The pressures in the two chambers will quickly equalize, and since the surface area of the top of the cylinder 40 and the interior of passageway 48 is much greater than the surface area at the bottom of the cylinder and above the ball, the cylinder will be driven downward. The downward motion is opposed by the force of the spring 46. However, the spring force at this time is not sufficient to halt the downward motion of the cylinder 40, and the cylinder will soon contact the ball 38 and press it against its valve seat 39, thereby sealing the passageway 36 and preventing further flow of gas into the lower chamber 47.

As the cylinder 40 moves downward the volume of the upper chamber 49 is increased, and the pressurized gas in the two chambers expands to fill this volume. The downward movement of the cylinder 40 will move the top of the cylinder and its O-ring 43 to a position below the intersection of a passageway 52 with the upper chamber 49. The passageway 52 conducts the gas to pressure distribution spool 50, at which time the gas expands further to fill passageway 52 and volume 54 around the spool. The effect of this expansion of the gas is to drop its pressurization in the expansion regions to an operating pressure of about 250 p.s.i. An equilibrium condition is reached with this pressure level existing in the upper and lower chambers 49 and 47, passageways 48 and 52 and the spool volume 54. At equilibrium the passageway 36 leading to the regulator will remain sealed by the ball 38, since the combination of the upward forces of 800 p.s.i. acting on the ball 38, the 250 p.s.i. pressure acting on the bottom of the cylinder 40, and the upward force of the spring 46 is still insufficient to overcome the downward force of 250 p.s.i. acting on the large surface area of the top of the cylinder 40 and on the interior surfaces of the central passageway 48.

When the 250 p.s.i. pressure in the volume 54 around the spool 50 is released during operation of the stapler, the 250 p.s.i. pressure acting on the top of the cylinder 40 is removed, and the forces of the spring 46 and the pressure on the ball 38 urge the cylinder upward. A plug 41 which seals the top of the regulator chamber limits the extent of upward travel of the cylinder 40 as shown in FIG. 4a. Pressurized gas once again begins to flow into the lower chamber 47 and the pressure regulation cycle repeats.

The pressure distribution spool 50 provides a means for applying pressurized gas at the regulated pressure to operative parts of the stapler during a stapling procedure. Pressurized gas is needed during two phases of operation. One is the clamping cycle, when tissue being stapled is clamped between the jaws or other opposing parts of the stapler head. The other is the stapling cycle, when staples are driven through the tissue.

The spool 50 is capable of movement within a spool chamber 56. Located around the spool 50 and above and below the volume 54 are O-rings 58 and 60 as shown in FIGS. 4a–4c. Extending upward from the main body of the spool is a stem 62 with a locking tab 64 located near the top of the stem. A slide latch 66 is located at the end of the stem 62. Extending downward from the spool body is a cam extension 68. A spring 69 is located in the spool chamber 56 above the main body of the spool, and is compressed as the spool moves upward in the chamber 56.

Interacting with the spool 50 and governing its sequence of operation are two firing sequencing mechanisms 70. Interacting with the stem 62 is a slide 72 which extends outward from the rear of the handle. The slide is spring-loaded so that when it is not latched or being pressed at its outward end 74, it will be urged outward as shown in FIG. 1. Interacting with the cam extension 68 of the spool is a pivoting trigger safety 76. The trigger safety can be manually moved in a safety guide slot 80 and the trigger safety 76 can be pivoted from alignment with the slot 80 to an extension 82 of the slot 80 when the stapler is to be fired to implant staples. A spring-loaded trigger 84 has a rearward projection 86 which opposes the cam extension and trigger safety mechanisms.

When the spool is located as shown in FIG. 2, a gas pressure of 250 p.s.i. is confined to the volume 54 around the spool. When the spool is raised so that the volume 54 opposes passageway 90 as shown in FIGS. 4a and 4b, pressurized gas flows from the volume 54 to the stapler head to clamp tissue in the head, since passageway 90 leads to the parallel union 120 and tubing segment 34. When the spool is raised further so that the volume 54 opposes passageways 90 and 92 as shown in FIG. 4c, the clamped tissue is stapled by reason of pressurized gas flow from the volume 54 through passageway 92 and to the stapling mechanism by way of the union 120 and tubing segment 32.

Initially, the spool cannot be moved in its chamber 56. This is because the central slot of the slide 72 through which the stem 62 of the spool extends is narrowed at the end as shown at 73 in FIGS. 2 and 3. When the stem 62 is positioned at the narrowed end of the slide 72, the outward extending locking tabs 64 of the stem abut against the bottom of the slide end, preventing any upward movement of the spool. The spool cannot move upward until the outer end 74 of the slide 72 is depressed, causing the narrowed end 73 to clear the tabs 64 so that the tabs are positioned in opposition to the wider central slot of the slide.

This safety feature remains operative until the user depresses the end 74 of the slide. As the slide 72 is depressed into the handle, the slide latch 66 at the top of the stem 62 rides upward along the angled upper surface 71 of the slide 72. This motion pulls the spool 50 upward so that the volume 54 opposes passageway 90. At the end of the depression of the slide the latch 66 snaps into a clamp notch 75 at the end of the angled surface 71, and the gas flowing to the stapler head through passageway 90 has clamped tissue in the stapler head for stapling. The spool 50 and slide 72 are then located as shown in FIG. 4a.

With the tissue clamped in the stapler head and the spool located as shown in FIG. 4a, the staples cannot as yet be implanted into the tissue by reason of the trigger safety mechanism. This is because the projection 86 of the trigger 84 is opposing the side of the cam extension 68. In order to fire the staples in the stapler head, the trigger safety 76 must be manually pushed upward in safety guide slot 80. This motion lifts the spool 50 slightly so that the extension cam 68 is in the firing position, shown in FIG. 4b. The trigger safety and spool will not remain in this position, however, because the trigger safety and spool will spring back downward if the trigger safety is released without being locked. Release of the trigger safety without locking allows the slide 72 to spring outward when the slide latch 66 is lifted above the clamp notch 75. The spool will then spring downward under the force of spring 69, and will push the trigger safety down as the cam extension 68 pushes against the trigger safety 76. This will release the clamped tissue in the stapler head as the pressurized gas in the clamping mechanism is released through passageway 90 into the spool chamber 56. The clamping and stapling process may then be begun anew.

However, if the user is satisfied with the clamping of the tissue in the stapler head, the staples may be implanted by sliding the trigger safety 76 upward and pivoting the safety into the slot extension 82, as shown in FIG. 4b. When this is done, the slide 72 is released from the slide latch 66, allowing the slide to spring outward, and the projection 86 of the trigger 84 opposes the junction of the trigger safety 76 and the cam extension 68. The volume 54 around the spool continues to pressurize the clamping mechanism, holding the tissue securely clamped in the stapler head.

When the trigger 84 is now depressed, the upper surface of the trigger projection 86 will contact the cammed bottom of the cam extension 68, causing the spool to move upward, as shown in FIG. 4c. As soon as this movement causes the volume 54 to oppose passageway 92, pressurized gas flows through this passageway to the staple implanting mechanism in the stapler head. Staples are thereby implanted in the clamped tissue.

As the trigger 84 is depressed, the surface 88 of the trigger below the projection 86 contacts the trigger safety 76 and pivots the safety out of the slot extension 82 and back to alignment with the guide slot 80 as shown in FIG. 4c. The trigger 84 is spring-loaded so that when it is released it moves back to its undepressed position. This enables the spool 50 to move back down under the force of its spring 69. As it does so, the cam extension 68 returns the trigger safety 76 to its initial downward position. As the spool moves down, passageway 92 and then passageway 90 are vented into the spool chamber 56 above the spool. Since this space is vented to atmospheric pressure, the gas pressure in the two passageways is thereby released. This venting of gas pressure releases the stapling and clamping mechanisms from the tissue. When the spool has reached the bottom of the chamber 56 the locking tabs 64 of the stem are again positioned beneath the narrowed end of the slide 72 to lock the spool in its original position, shown in FIG. 2. Volume 54 is repressurized with gas from the regulator 30, and the stapler is ready for the next stapling procedure.

Figure 5:
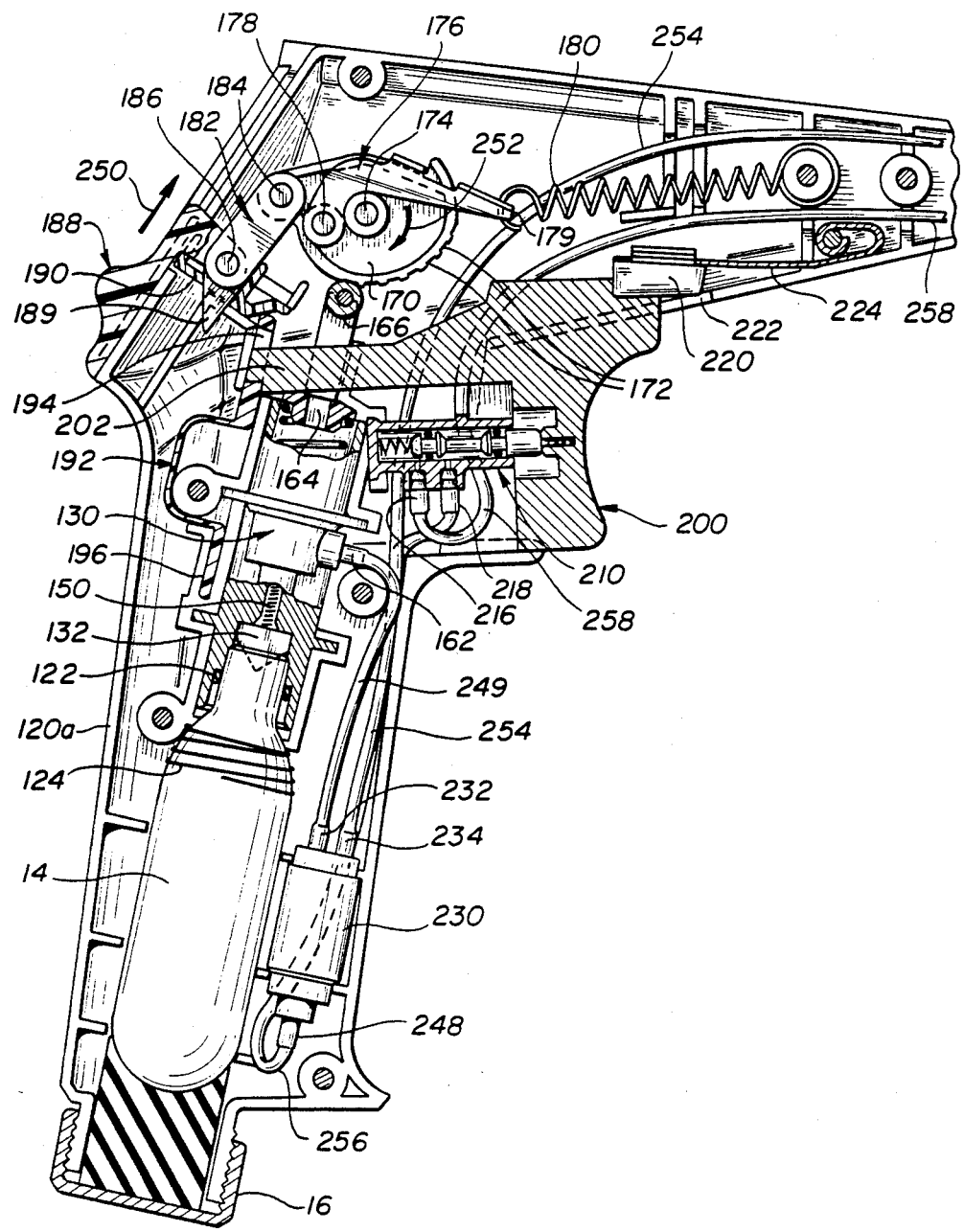
FIG. 5 illustrates a second embodiment of a surgical stapler constructed in accordance with the principles of the present invention.
Figure 6:
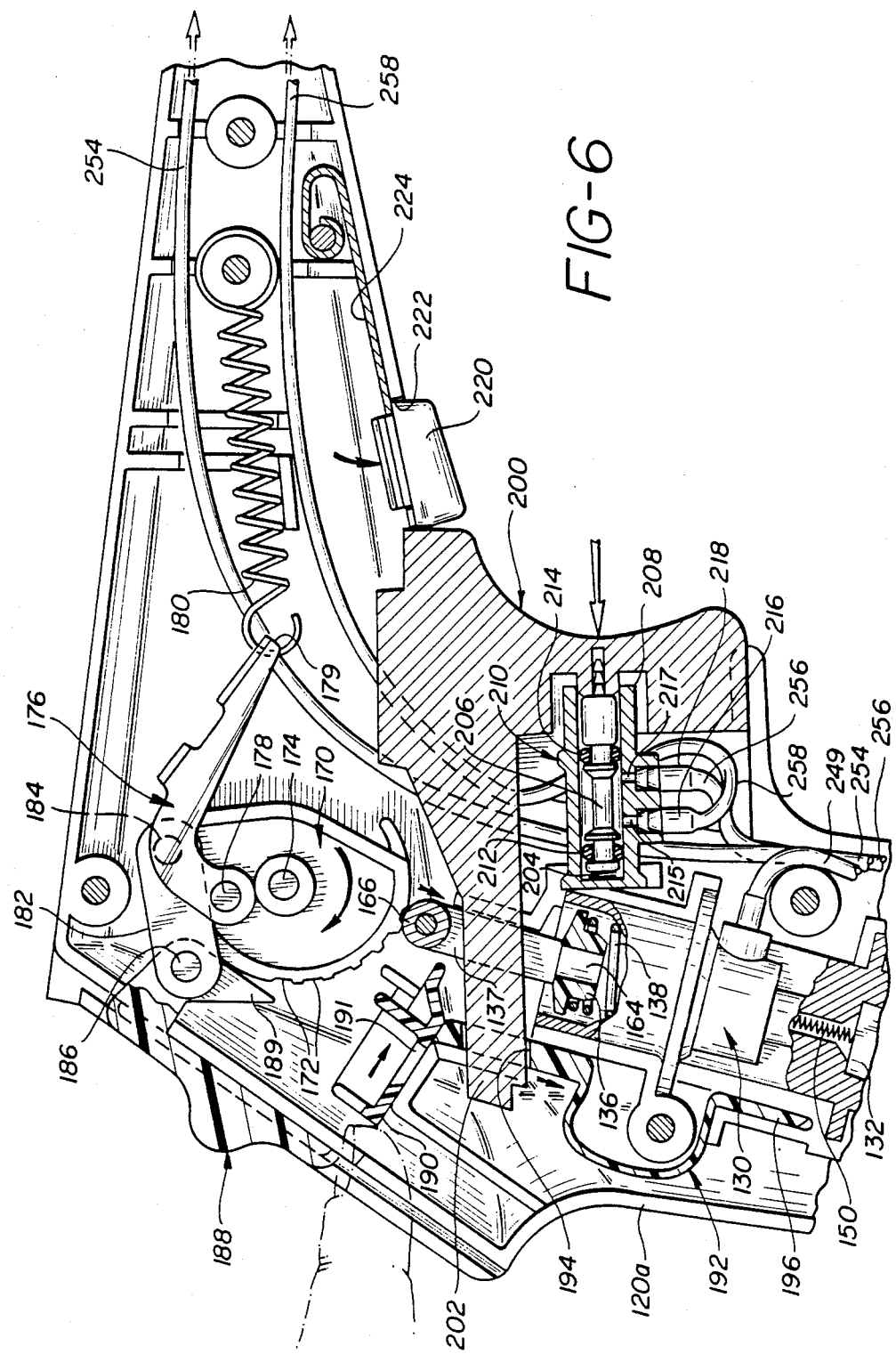
FIG. 6 illustrates the stapler of FIG. 5 following actuation.

Referring to FIGS. 5 and 6, a second embodiment of a surgical stapler constructed in accordance with the principles of the present invention is shown. In this embodiment the gas cylinder 14 is inserted into the handle 120 of the stapler. An O-ring 122 provides a seal around the neck of the cylinder 14 and a coil spring 124 is located just below the neck of the cylinder. The coil spring 124 urges the cylinder away from the piercing blade 132 prior to tightening of the cap 16. The spring 124 thus prevents puncture of the cylinder by the blade 132 during shipping and handling of the stapler. The cap 16 is not tightened until it is desired to use the stapler, at which time the tightening of the cap punctures the cylinder, releasing high pressure gas into the pressure regulator 130.

Figure 7:
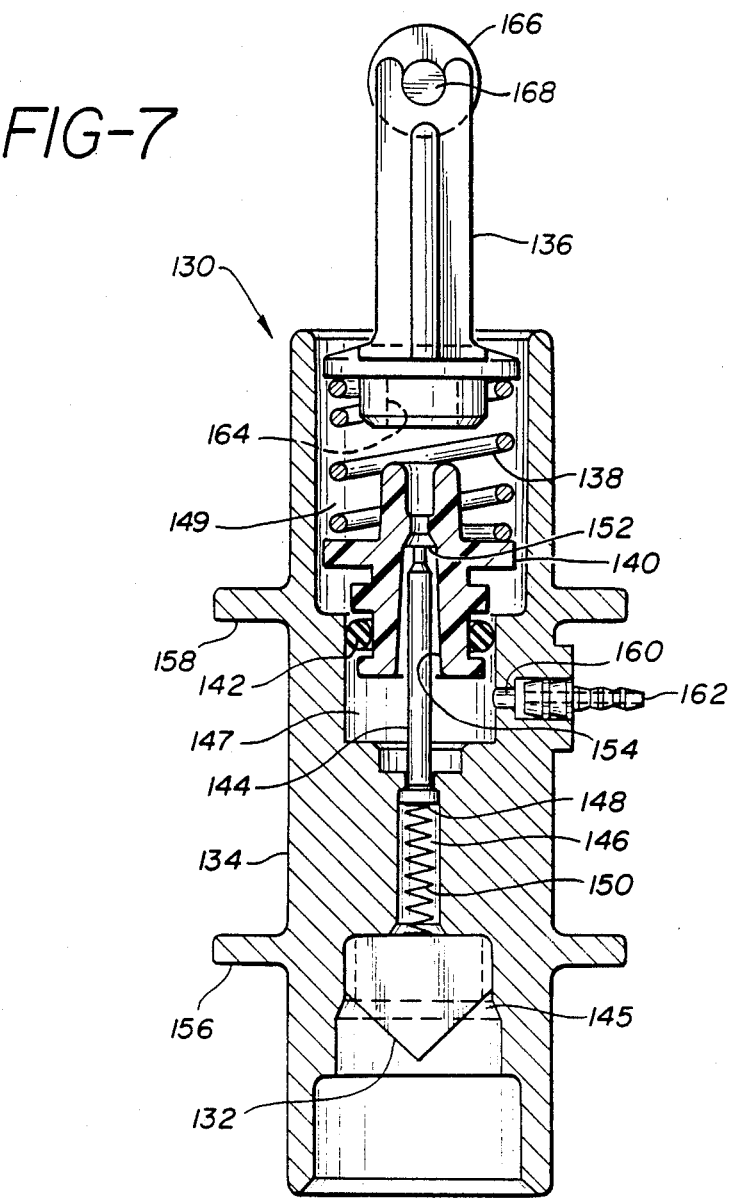
FIGS. 7 and 8 illustrate the variable pressure regulator of the stapler of FIG. 5 at two different phases of operation.

Referring concurrently to FIG. 7, the regulator includes an outer cylindrical housing 134 and a movable plunger 136. A spring 138 is located between the plunger 136 and a piston 140. An O-ring 142 provides a seal around the piston 140. A pin 144 is located to extend from a lower passageway 146 of the regulator housing with the head 148 of the pin seated at the top of the passageway. A light spring 150 (e.g., with a force of one pound or less) is located in the passageway 146 between the blade 132 and the head of the pin to hold the pin up in the passageway. The upper end of the pin 144 is bevelled to a narrow diameter tip with the bevel of the pin being positioned on a seat 152 formed in a passageway 154 extending through the piston.

The regulator housing has two outwardly extending flanges 156 and 158 which fit into mating openings in the surrounding internal walls of the handle 120. The interior of the regulator housing is divided into four spaces, generally demarcated by the flange positions. The lower space 145 below the position of flange 156 engages and surrounds the pierced end of the gas cylinder 14. The piercing blade 132 is force fit into the top of this space 145. The space above the lower flange 156 contains high pressure gas and comprises the passageway 146, occupied by the spring 150 and the head 148 of the pin 144. Above the seated head of the pin is a larger diameter space 147 which engages the lower portion of the regulator piston. Gas at the desired regulated pressure is contained within this space 147. Above the upper flange 158 is a cylindrical space 149 containing the upper portion of the piston, the spring 138, and the plunger 136. This space 149 is at ambient pressure, and is vented through a passageway 164 of the plunger 136.

Located between the upper prongs 137 of the plunger 136 is a roller 166 which is mounted on a shaft 168. The cylinder rolls against the surface of an opposing cam 170, which rotates on a pivot shaft 174. The surface of the cam which engages the roller 166 contains shallow depressions to provide detents for the roller. A double J-hook 176 is pivotally mounted to the cam 170 by a pivot pin 178. The right J-hook is visible in FIG. 5, with the left J-hook mounted in parallel and behind the right J-hook in this view. The forward-most end 179 of the J-hook is connected to the handle by a heavy spring 180.

The cam 170 is pivotally connected to an H-link 182 by a pivot pin 184. The H-link is also pivotally connected to an extension of a slide button 188 by a second pivot pin 186. A trigger safety slide 190 is slideably mounted behind the slide button and contains an opening 191 which is engaged by a pointed extension 189 of the slide button 188. The angled, forward-most end of the trigger safety slide opposes the top of a leaf spring 192. The lower end 196 of the leaf spring is affixed to the handle 120, and an opening 194 at the top of the leaf spring engages the rear extension 202 of a trigger 200.

The trigger 200 is slideably mounted and extends from the front of the hand-grip of the handle. The trigger is spring-loaded by a spring 204 to return to its outward position after firing and unlocking, as explained below. The trigger includes a rearward extension 202 which is notched at the end. The rearward extension of the trigger passes between the two upward extending sides of the plunger and the notched end of the extension engages the opening 194 of the leaf spring 192. Extending rearward from the finger grip of the trigger 200 is a shaft 206, which forms a part of a pneumatic valve 210. The shaft 206 is surrounded by two O-rings 212 and 214 and slides within a housing 208 of the pneumatic valve 210. The end of the shaft 206 engages the trigger return spring 204 as the shaft slides within the pneumatic valve housing 208. The housing 208 is open to atmospheric pressure at the rearward end to vent gas from the stapling mechanism. Two fittings 216 and 218 are connected to ports 215 and 217 for the passage of gas through the pneumatic valve. A trigger locking button 220 is located above and partially forward of the trigger. The locking button is slideably mounted in an opening 222 of the handle and is urged downward by a leaf spring 224.

Figure 9:
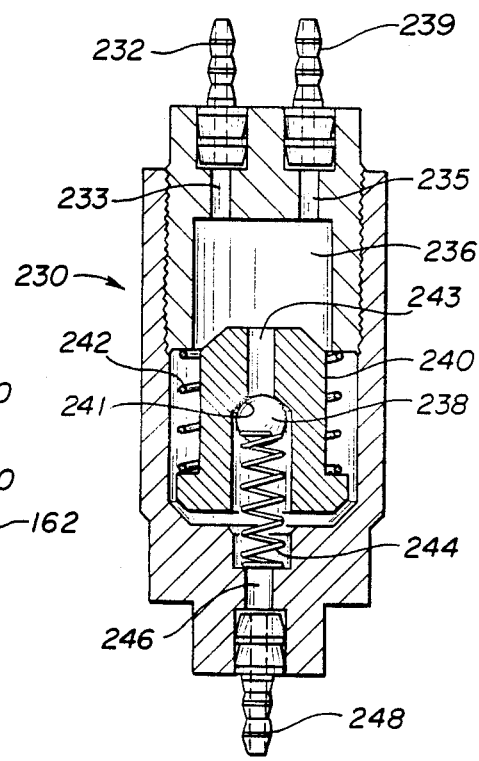
FIG. 9 illustrates the check valve of the stapler of FIG. 5.

Also located in the handle 120 is a check valve 230. Referring concurrently to FIG. 9, the check valve 230 has two fittings 232 and 234, the former connected to the outlet fitting 162 of the pressure regulator by tubing 249 and the latter being connected to the clamping mechanism in the stapler head by tubing (not shown). The fittings 232 and 234 are connected to ports 233 and 235 which lead to an interior chamber 236 of the check valve. Located within the chamber 236 is a cylinder 240 with a central passageway 243 that is narrowed in diameter to provide a valve seat for a ball 238. A spring 244 urges the ball upward in the cylinder passageway. An outer spring 242 surrounds the cylinder and presses downward against a flange at the base of the cylinder. At the bottom of the chamber 236 is a port 246 leading to a fitting 248. The fitting 248 is connected by tubing (not shown) to the inlet fitting 218 of the pneumatic valve 210 of the trigger 200.

In operation the gas cylinder 14 is located inside the handle and the cap 16 is tightened to force the cylinder upward, piercing the top of the cylinder and releasing high pressure gas into the pressure regulator. The presence of the pressurized gas may be indicated by an indicator such as indicator 20, shown in FIG. 3. At this time the gas pressure at the regulator outlet fitting 162 remains at atmospheric pressure.

The tissue to be stapled is now located between the operating members of the stapling mechanism for clamping. To clamp the tissue, the user slides the slide button 188 upward along the rear of the stapler handle, as indicated by arrow 250. The upward motion of the slide button lifts the connected H-link 182, thereby pivoting the cam 170 as indicated by arrow 252. As the cam rotates it presses the plunger 136 of the regulator 130 downward, increasing the force of the spring 138 against the piston 140 and driving the piston downward. As the piston moves down, it seats the top of the pin 144 on the seat 152 and presses the pin down, thereby unseating of the head 148 of the pin and releasing high pressure gas into the central space 147. The pressurization of this space presses upward against the piston to reseat the head of the pin and the pressure equalizes throughout the space 147. As the cam continues to rotate the pressurization of space 147 continues as the regulated pressure in the space builds. This regulated pressurized gas passes through the port 160 and outlet fitting 162, and through the tubing 249 to the inlet fitting 232 of the check valve 230. The gas then passes through the interior chamber 236 of the check valve and out the fitting 234 to the clamping mechanism in the stapler head. Thus, the clamping force is gradually increased as the slide button moves upward.

It may be appreciated that the sliding of the slide button 188 is opposed by the pressures and forces existing and developed in the regulator which tend to oppose the rotation of the cam and the downward motion of the plunger. The purpose of the J-hook 176 and its heavy spring 180 is to provide an assist toward neutralizing these opposing forces. It may be seen that initially the pivot pin 178 of the J-hook is below a line drawn between the cam shaft 174 and the handle anchor point of the spring 180. The initial motion of the slide button will rotate the location of the pivot pin above this line, however, whereafter the moment arm exerted by the spring and J-hook at the pivot pin 178 will provide a torque in the direction of the arrow 252. Thus, shortly after the slide button begins its upward travel the torque supplied by the J-hook will steadily increase at the same time as the expansive forces in the regulator are increasingly opposing this travel.

The gas that pressurizes the interior chamber of the check valve also enters the cylinder 240 in the check valve through the central passageway 243 of the check valve. The gas flows around the check valve ball 238 and out through the port 246 and the outlet fitting 248 to the inlet fitting 218 of the pneumatic trigger valve 210. Thus, pressurized gas is now present in the trigger valve 210 for the subsequent stapling operation.

If the operator finds that the clamping procedure is not to his liking, the tissue may be readily unclamped by sliding the slide button 188 down again. This action reverses the rotation of the cam 170, allowing the plunger 136 and the piston 140 to move upward under the pressure of the gas in the space 147. Pressurized gas bleeds out through the passageway 154 of the piston as the bevelled tip of the pin 144 periodically unseats from the seat 152. Eventually the head of the pin will seat to prevent the entry of high pressure gas into the space 147 and the upper tip of the pin will unseat at 152, thereby venting the remaining pressurized gas in space 147 through the passageway 154 of the piston and the plunger passageway. Thus the clamping force is removed from the clamping mechanism by this venting of gas through the regulator 130.

Once the user has clamped the tissue to be stapled to his liking, the trigger must be depressed to staple the tissue. However, an interlock mechanism must be activated before the trigger can be depressed. It may be seen in FIG. 5 that the trigger cannot be depressed due to the engagement of the notched end of the trigger extension 202 with the leaf spring 192. In addition, stapling must not take place until the pneumatic trigger valve is fully pressurized to the proper stapling pressure.

The regulator components including the spring 138 and the cam are arranged so that a proper stapling pressure of 250-300 p.s.i. is not attained until the slide button 188 has been moved fully to the top of the rear of the handle. Only when the slide button is so positioned will the slide button clear an underlying aperture in the handle through which the trigger safety slide 190 may be accessed. The accessible safety slide 190 is depressed, and its leading angled edge presses against the upper end of the leaf spring 192, thereby pressing the leaf spring downward. The downward movement of the leaf spring releases the lower edge of the leaf spring 192 from the notch in the trigger extension 202, and the trigger extension may now move rearward through the opening 194 when the trigger is depressed.

Before the trigger is depressed, pressurized gas at the stapling pressure of 250-300 p.s.i. is located in the space around the shaft 206 of the trigger valve, between the O-rings 212 and 214. When the trigger is depressed the shaft 206 moves rearward so that this space overlies the inlet port 217 and the outlet port 215, thereby allowing gas to flow between the two ports. This pressurized gas at the desired stapling pressure passes out through the fitting 216 to the stapling mechanism in the stapler head, thereby implanting the staples in the clamped tissue.

When the trigger 200 is depressed the trigger clears the trigger locking button 220 which is located above the leading upper edge of the trigger. As the trigger clears the locking button the button snaps downward from the opening 222 under the force of the leaf spring 224, thereby locking the trigger in its actuated position. The appearance of the locking button, which is preferably distinctly colored, also visually informs the user that the stapler has been fired and cannot be used again until it has been properly reset and reloaded with staples. Pressurized gas at the stapling pressure is at this time maintained in both the clamping and stapling mechanisms in the stapler head. At this point, the components in the handle are oriented as shown in FIG. 6.

After the stapling procedure is complete it is necessary to release the stapling head from the clamped tissue. To do so, the handle mechanisms must be reset. These mechanisms interact so as to insure that the instrument is fully reset and cannot be used again until the instrument has been fully readied for another stapling procedure.

The first step in releasing the clamped tissue is to slide the slide button 188 down to its initial position. This vents the gas in the clamping mechanism back through the interior chamber 236 of the check valve, through the tubing 249, and through the passageways 154 and 164 in the regulator cylinder and plunger. This venting of gas pressure releases the stapler from the stapled tissue. As the slide button 188 returns to its initial position, the pointed extension 189 of the slide button engages the opening 191 of the trigger safety slide, thereby moving the safety slide rearward to its initial position. The leaf spring 194 springs upward so that reextension of the trigger will again cause the leaf spring to block inadvertent actuation of the trigger.

At this point a user may set the stapling instrument aside, forgetting to reset the trigger mechanism. To guard against this possibility, the check valve 230 acts to maintain a low pressure at the stapling mechanism, on the order of 50 p.s.i., after the clamping pressure has been released and before the trigger is reset. This low pressure will act to keep the staple driver in the stapling mechanism extended into the spent staple cartridge. With the staple driver so extended, it is not possible to remove the spent staple cartridge from the stapler head.

To reset the trigger, the trigger locking button 220 must be pressed upward into the opening 222 in the handle. This will allow the trigger 200 to spring forward under the force of the spring 204. The shaft 206 of the pneumatic valve will then return to its initial position, and gas pressure in the stapling mechanism will be vented through the fitting 216, port 215, and the rear of the valve housing 208 behind the shaft 206. The release of gas pressure allows the staple driver to retract from the staple cartridge so that the cartridge may be removed from the stapler head. The rearward extension 202 of the reset trigger will be locked by the leaf spring 192 and the trigger locking button will be supported in its retracted position in the opening 222 above the trigger. The stapling instrument is thus fully reset and ready to be reloaded with a new staple cartridge in preparation for the next stapling procedure.

Figure 8:
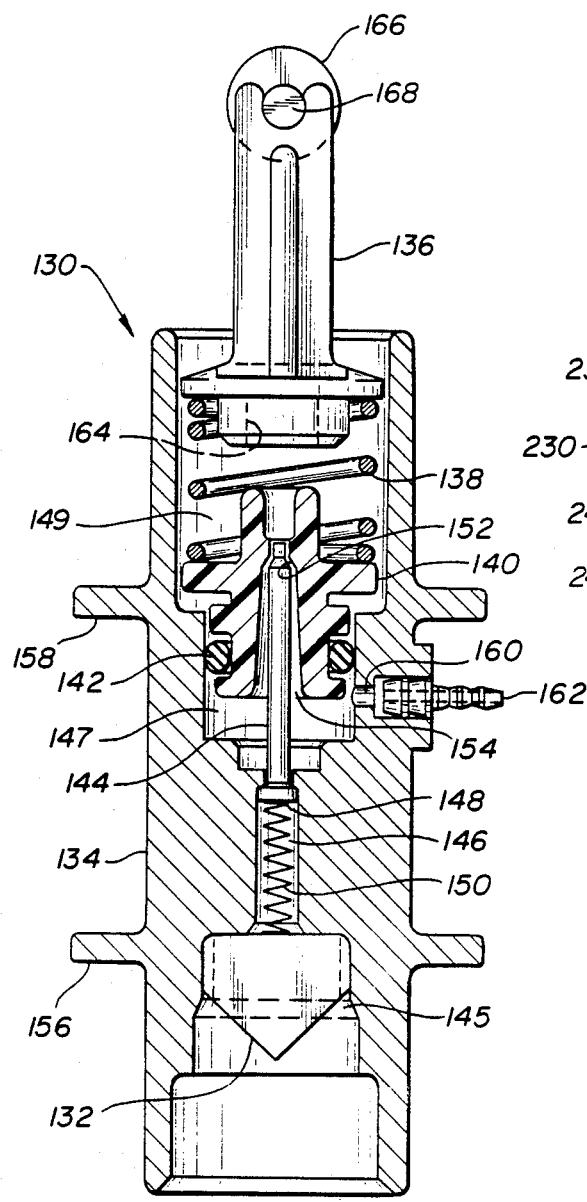

The operation of the variable pressure regulator may be more fully understood with reference to the enlarged views of the regulator 130 of FIGS. 7 and 8. In FIG. 7 the regulator is shown prior to the application of pressurized gas to the regulated gas space 147. At this time high pressure gas from the gas cylinder 14 is released by the piercing blade 132 and fills the lower space 145 and the lower passageway 146 below the pin 144. This gas pressure keeps the head 148 of the pin seated against the upper, narrower diameter portion of passageway 146 above the head of the pin. With the slide button now at its lowermost position, the plunger 136 is located by the cam at its uppermost position in the upper space 149. The minimal pressure exerted on the piston 140 by the spring 138 at this time is insufficient to fully seat the bevelled tip of the pin against the piston seat 152, as exaggerated in the view of FIG. 7. Thus, at this time there is a pathway for atmospheric pressure from the outlet fitting 162 through the port 160, through the space 147, through the passageway 154 in the center of the piston and around the tip of the pin, through the upper space 149 and out through the passageway 164 through the center of the plunger 136.

FIG. 8 shows the variable regulator 130 as it is developing regulated gas pressure in the central space 147. As compared to FIG. 7, the plunger 136 is now pressed downward by the cam, compressing the spring 138 against the piston 140. This downward motion of the piston seats the bevelled tip of the pin 144 on the seat 152 in the piston, unseating the head of the pin and allowing high pressure gas to flow into the central space 147. As the gas pressure equalizes and urges the piston upward against the force of spring 138 the head of the pin reseats and prevents any further high pressure gas from entering the space 147. Continual downward movement of the plunger will cause increments of high pressure gas to enter space 147 with the position of the piston remaining essentially unchanged as the regulated gas pressure equalizes the force of the spring 138. In this way regulated pressurized gas is developed in the space 147 over a pressure range of zero to the operating pressure of the stapling mechanism.

The check valve 230 is shown in the enlarged cross-sectional view of FIG. 9. The check valve regulates the flow of pressurized gas to and from the stapling mechanism, and is essentially a pass-through for gas to the clamping mechanism. Pressurized gas is supplied to the check valve through the inlet fitting 232 and port 233, filling the interior chamber 236 with gas. The gas in the chamber flows unimpeded through the outlet port 235 and fitting 234 to the clamping mechanism. Thus, the clamping pressure is directly related to the regulated pressurized gas developed by the regulator 130.

The pressurized gas in the inlet chamber 236 unseats the ball 238 from its valve seat 241 in the cylinder 240. As the ball is urged downward by the gas, the gas flows around the ball, through the cylinder passageway 243, and through the port 246 and the fitting 248 to the pneumatic trigger valve 210. Eventually the gas pressure inside the valve will reach the maximum (stapling) pressure, and this pressure will be present throughout the check valve.

When the slide button 188 is moved downward to release the clamping mechanism the pressurized gas in the clamping mechanism is vented back through the fittings 234 and 232 and the regulator 130. The gas pressure in the interior chamber 236 is thereby reduced to zero pressure. The pressurized gas in the stapling mechanism at this time also declines as gas is vented through the pneumatic trigger valve 210, the fitting 248 and the port 246. This pressure of the venting gas will push the ball 238 upward, sealing the central passageway of the cylinder 240 as the ball seats on the valve seat 241. With the central passageway sealed, the pressurized gas will urge the cylinder 240 upward in the check valve against the force of the surrounding spring 242. Gas from the stapling mechanism is thus vented around the cylinder 240 and through the space in which the spring 242 is located. This venting of gas continues until the gas pressure in port 246 drops to around 50 p.s.i. At this lowered pressure the force of the spring 242 overcomes the gas pressure and the spring 242 will force the cylinder 240 downward in the interior chamber of the check valve, seating the bottom of the cylinder against the bottom of the chamber. This closure of the ball 238 against its seat 241 and the seating of the cylinder 240 against the bottom of the check valve chamber traps gas at approximately 50 p.s.i. at the outlet port 246, thereby maintaining this pressure at the stapling mechanism until the trigger is reset to vent the remaining gas pressure in the stapling mechanism through the rear of the pneumatic valve. The staple cartridge may then be removed and replaced as discussed above.

what is claimed is:

1. A surgical stapling instrument including a handle, a stapler head having a clamping mechanism and a stapling mechanism, and means interconnecting said handle and said stapler head comprising:
    a source of pressurized gas having an outlet;
    means, in fluid connection with said outlet, for controllably supplying pressurized gas to said clamping mechanism and said stapling mechanism; and
    indicator means in fluid connection with said outlet, for providing an indication of the presence of pressurized gas in said instrument, wherein said indicator means includes a movable member, spring-biased against the force of pressurized gas present in said instrument, said movable member being movable in response to the force of pressurized gas to indicate the presence of pressurized gas in said instrument.

2. The surgical stapling instrument of claim 1, wherein said movable member extends from the surface of said instrument in response to the presence of pressurized gas, and wherein an extending portion of said movable member is distinctly colored.

3. A surgical stapling instrument comprising:
    a handle containing a source of pressurized gas;
    a stapler head having a clamping mechanism and a stapling mechanism;
    means connecting said handle and said stapler;
    means, coupled to said gas source for regulating gas at a lower pressure than provided by said source;
    means for controllably supplying pressure regulated gas to said clamping mechanism and said stapling mechanism;

wherein said clamping mechanism includes a movable clamping member and said stapling mechanism includes a staple magazine having a plurality of staples, a plurality of drivers for driving said plurality of staples, said drivers operable by supplying pressure regulated gas to said rivers, and a plurality of anvils corresponding to said plurality of staples for clinching said staples after being expelled from said staple magazine by said drivers.

4. The surgical stapling instrument of claim 3, wherein said regulating means comprises a pressure regulator including:

an outer compartment having an inlet port for receiving pressurized gas from said source and an outlet port; and an inner movable member disposed between said inlet and outlet ports which is selectively movable to admit the passage of gas between said source and said outlet port, whereby pressure regulated gas is developed at said outlet port.

5. The surgical stapling instrument of claim 4, wherein said inner movable member is spring-loaded for regulation of the developed gas pressure.

6. The surgical stapling instrument of claim 5, wherein said inner movable member includes a generally cylindrical piston having a passageway passing therethrough to conduct gas between said inlet and outlet ports; and valve means for selectively occluding said inlet port.

7. The surgical stapling instrument of claim 6, wherein said valve means comprises a ball valve controlled by movement of said piston.

8. The surgical stapling instrument of claim 4, further comprising a spool valve having an inlet coupled to the outlet port of said pressure regulator, a first outlet coupled to said clamping mechanism and a second outlet coupled to said stapling mechanism, and a valve member movable to a first position for coupling said inlet to said first outlet and a second position for coupling said inlet to said second outlet.

9. The surgical stapling instrument of claim 8, wherein said valve member couples said inlet to said first and second outlets when moved to said second position.

10. The surgical stapling instrument of claim 9, further comprising a manual control for moving said valve member to said first position and a trigger mechanism for moving said valve member to said second position, wherein said valve member is further movable to a third position in which said inlet is connected to neither said first or second outlet.

11. The surgical stapling instrument of claim 10, wherein said spool valve further includes means for preferentially moving said valve member to said third position.

12. The surgical stapling instrument of claim 11, wherein said manual control comprises a spring-loaded slider.

13. The surgical stapling instrument of claim 12, wherein said manual control further comprises means for retaining said valve member in said third position prior to actuation of said manual control.

14. The surgical stapling instrument of claim 4, wherein said inner movable member comprises means for variably controlling the gas pressure at said outlet port.

15. The surgical stapling instrument of claim 14, wherein said variably controlling means includes a movable piston, a valve operatively ConneCted to said piston, and means for applying a variable force to said piston in opposition to gas pressure.

16. The surgical stapling instrument of claim 15, wherein said variable force is applied to one side of said piston and said outlet port is located on an opposite side of said piston.

17. The surgical stapling instrument of claim 16, wherein said piston includes valve means for venting pressurized gas from said outlet port.

18. The surgical stapling instrument of claim 14, wherein said variably controlling means includes a movable piston opposing said outlet port on one side;

a spring opposing the opposite side of said piston;

a movable cam;

a cam follower for connecting said spring and said cam; and control means for controlling the position of said cam.

19. The surgical stapling instrument of claim 3, wherein said regulating means includes an outlet port at which pressure regulated gas is developed, and wherein said gas supplying means includes:

means for coupling said outlet port to said clamping mechanism; and trigger means for controllably supplying gas developed at said outlet port to said stapling mechanism.

20. The surgical stapling instrument of claim 19, wherein said trigger means includes a pneumatic valve having an inlet coupled to said outlet port and an outlet coupled to said stapling mechanism, whereby actuation of said trigger means establishes a fluidic connection between said inlet and said outlet of said pneumatic valve.

21. The surgical stapling instrument of claim 20, further comprising a check valve having an inlet coupled to said outlet port an outlet coupled to said inlet of said pneumatic valve, and a valve member biased to pass pressure regulated gas from said check valve inlet to said check valve outlet.

22. The surgical stapling instrument of claim 21, wherein said valve member of said check valve is further biased to maintain pressurized gas at the outlet of said check valve upon the removal of pressurized gas from the inlet of said check valve.

23. The surgical stapling instrument of claim 21, wherein said check valve further includes a second outlet, and wherein said means for coupling said outlet port to said clamping mechanism includes said inlet and said second outlet of said check valve, wherein said second outlet of said check valve is coupled to said clamping mechanism.

* * * * *

UNITED STATES PATENT AND TRADEMARK OFFICE
CERTIFICATE OF CORRECTION

PATENT NO. : 4,951,861

DATED : August 28, 1990

INVENTOR(S) : Dale Schulze; Bela Vincze; James Bedi; Jess Deniega; Jack Pedlick and William Fox It is certified that error appears in the above-identified patent and that said Letters Patent is hereby corrected as shown below:

Column 13, line 6 "rivers" should be "drivers".

Signed and Sealed this

Thirty-first Day of December, 1991

Attest:

HARRY F. MANBECK, JR.

*Attesting Officer*      *Commissioner of Patents and Trademarks*